(12) United States Patent
Fischer et al.

(10) Patent No.: US 8,968,647 B2
(45) Date of Patent: Mar. 3, 2015

(54) FRAGRANCE DELIVERY SYSTEM

(71) Applicants: Albert Michael Fischer, Fairfield, OH (US); Matthew Thomas Kuhn, Cincinnati, OH (US); Robert Richard Ziek, Jr., Cincinnati, OH (US); Robert St Clair Donovan, Admas, NY (US)

(72) Inventors: Albert Michael Fischer, Fairfield, OH (US); Matthew Thomas Kuhn, Cincinnati, OH (US); Robert Richard Ziek, Jr., Cincinnati, OH (US); Robert St Clair Donovan, Admas, NY (US)

(73) Assignee: Julius Sämann Ltd., Hamilton (BM)

( * ) Notice: Subject to any disclaimer, the term of this patent is extended or adjusted under 35 U.S.C. 154(b) by 163 days.

(21) Appl. No.: 13/734,139

(22) Filed: Jan. 4, 2013

(65) Prior Publication Data

US 2014/0193295 A1 Jul. 10, 2014

(51) Int. Cl.
| | | |
|---|---|---|
| *A61L 9/00* | (2006.01) | |
| *A24F 25/00* | (2006.01) | |
| *B65D 73/00* | (2006.01) | |
| *B65B 41/18* | (2006.01) | |
| *B29D 22/00* | (2006.01) | |
| *A47G 19/00* | (2006.01) | |
| *A61L 9/12* | (2006.01) | |

(52) U.S. Cl.
CPC ............... *A61L 9/12* (2013.01); *Y10S 428/905* (2013.01)
USPC ............. 422/5; 422/306; 239/34; 206/484; 53/266.1; 53/467; 428/34.1; 428/35.7; 428/905; 220/23.83

(58) Field of Classification Search
CPC .......... A01N 1/0215; A61L 2/00; A61L 9/00; A61L 9/01; B32B 3/00; B65D 2575/00; B67D 1/0443
USPC .......... 422/5, 28, 305–306; 239/34; 206/484; 53/467, 111 RC, 170, 558, 266.1; 428/34.1, 35.7, 905; 220/23.83
See application file for complete search history.

(56) References Cited

U.S. PATENT DOCUMENTS

| 2,629,628 A | | 2/1953 | Vaillacourt | |
|---|---|---|---|---|
| 4,145,001 A | * | 3/1979 | Weyenberg et al. | ............ 239/56 |
| 4,419,395 A | | 12/1983 | Sugimoto | |

(Continued)

FOREIGN PATENT DOCUMENTS

| EP | 1 704 874 A1 | 9/2006 |
|---|---|---|
| WO | WO 93/00115 | 1/1993 |
| WO | WO 03/097114 A1 | 11/2003 |

OTHER PUBLICATIONS

International Search Report and Written Opinion issued Apr. 16, 2014 in PCT/US14/10154 with Search History.

*Primary Examiner* — Monzer R Chorbaji
(74) *Attorney, Agent, or Firm* — Oblon, McClelland, Maier & Neustadt, L.L.P.

(57) ABSTRACT

A multi-layer article is provided containing a sorbent layer having a first side and a second side; a vapor permeable or microporous layer adjacent to at least a portion of at least one of the first side and second side of the sorbent layer; optionally, a second vapor permeable or microporous layer on a side of the vapor permeable or microporous layer not adjacent to the sorbent layer; optionally, a vapor impermeable layer adjacent to a portion of the sorbent layer not adjacent to the vapor permeable or microporous layer; and an active composition having at least one volatile component; wherein the sorbent layer contains the active composition, and each layer is capable of being formed into a required shape or structure; and a method for its use in treating the atmosphere of an environment such as a compartment or localized space.

23 Claims, 5 Drawing Sheets

(56) References Cited

U.S. PATENT DOCUMENTS

| | | |
|---|---|---|
| 4,761,324 A | 8/1988 | Rautenberg et al. |
| 5,282,571 A | 2/1994 | Smith et al. |
| 5,820,791 A | 10/1998 | Canale |
| 6,013,589 A | 1/2000 | DesMarais et al. |
| 6,085,026 A | 7/2000 | Hammons et al. |
| 6,938,832 B2 | 9/2005 | Sada |
| 7,159,792 B2 | 1/2007 | Wheatley et al. |
| 8,043,569 B2 | 10/2011 | Tranzeat |
| 2002/0039869 A1 | 4/2002 | Achille |
| 2008/0105760 A1 | 5/2008 | Sheffield et al. |
| 2009/0072045 A1 | 3/2009 | Wheatley et al. |
| 2010/0065654 A1 | 3/2010 | Wheatley et al. |
| 2011/0108632 A1 | 5/2011 | Brandenburg et al. |
| 2012/0067970 A1 | 3/2012 | Hossein |

\* cited by examiner

FRAGRANCE DELIVERY SYSTEM

FIELD OF THE INVENTION

This invention is directed to an economical and effective fragrance delivery system that can be used to deliver aromachemicals or other volatile materials to a local environment. The system has a capacity to be effective for up to two months or longer and to provide a constant olfactive effect throughout the lifetime of performance.

BACKGROUND OF THE INVENTION

Myriad types of fragrance delivery systems are available on the market. Each system is designed to deliver a volatile chemical to a local environment, and, in general, conventional air freshener articles are constructed based on an article engine, where a volatile chemical composition is contained in a reservoir and emitted from the reservoir, either by the natural volatilization process or by a positive-forced emission, and where the volatile chemical composition is exposed to a source of heating or a forced stream of air to promote emission to the environment. Such systems vary in simplicity of design. Much more complex systems contain separate compartmentalized reservoirs of volatile chemicals, wherein volatilization and delivery into the environment are mechanically controlled and driven.

Generally, the chemical composition contained in a fragrance delivery system is described as a perfume, and a perfume can be any chemical or mixture of chemicals that upon volatilization either as a vapor or as microdispersed droplets, delivers an attractive or pleasing odor to a localized space. The technology of perfume composition creation is well known and described in the literature, such as, the book by S. Arctander, *Perfume and Flavor Chemicals* (1969, Montclair, N.J., USA). Also, there is an abundant wealth of patent literature available in the field of perfumery.

Conventionally, a perfume or chemical fragrance composition contains a complex mixture of volatile ingredients of natural or synthetic origin belonging to various chemical classes of compounds, including alcohols, aldehydes, ketones, esters, ethers, acetates, nitriles, terpene hydrocarbons, nitrogen or sulfur heterocyclic compounds and essential oils. These volatile materials, often characterized as aromachemicals may be compounded in a supporting chemical base that includes solvents and other ingredients selected depending upon the specific utility to which the final composition is directed. The final fragrance composition is often a complex mixture of multiple aromachemicals dissolved or dispersed in a carrier solvent base, which may be a mixture of solvent and volatile assistants compounded to optimize the release of the fragrance to the environment.

In most cases, the ideal goal of the fragrance delivery system is to provide a consistent release of the fragrance over the scheduled lifetime of the air freshener article. Such consistent release is herein referred to as a "linear release" and is employed to describe a concept whereby a consumer perceives the emitted scent from the article to be identical from a standpoint of quality and intensity throughout the prescribed lifetime of the article. In practicality, this ideal is difficult to achieve because aromachemicals of the fragrance composition have differing vapor pressures and differing threshold values at which a person perceives the odor of the aromachemical. Additionally, and important to the design of the aroma release engine system, consumers have differing abilities to detect the various aromachemicals, and this issue is compounded by effects of differing environmental conditions, i.e., temperature, air flow, humidity, volume of emission space, in which the fragrance dispenser is located.

Against such a complex set of issues, there have been many attempts to provide a fragrance release system that is simple in design, and reasonably low in cost yet effective in provision of a linear performance of perceived air-freshening effect.

U.S. Pat. No. 2,629,628 (Vaillancourt) (Feb. 24, 1953) describes an insect repellant attachment to be placed on a screen door. The device is constructed of a planar base of a suitable material such as heavy cardboard and a pad of absorbent material secured to the pad. The base extends beyond the pad in at least one direction and includes an eyelet or hole for insertion of a looped cord, which allows for hanging the device from a nail or hook on the screen door. The pad is saturated with the repellant, which upon normal opening and closing motion of the door, is dispersed from the pad.

U.S. Pat. No. 4,419,395 (Sugimoto) (Dec. 6, 1983) describes a perfumed pendent having a three-dimensional configuration. The pendant is constructed of a front vinyl sheet printed with a design and a back vinyl sheet mated to the front sheet, and the two sheets are welded to one another along an outer peripheral edge. A foam pad is interposed between the sheets to provide three-dimensional form. A capsulated perfume layer is laminated to the outer surface of the front sheet. The capsulated perfume layer contains a plurality of capsules containing perfume which are secured to the sheet surface by a binder. The perfume is released via scratching of a finger, for example.

WO 93/00115 (Fischel-Ghodsian) (Jan. 7, 1993) describes a device for controlled release of vaporous medications or repellants that is a multilayered laminate having, in order from the rear, an adhesive layer for fixing the device to a surface, an impermeable membrane layer, a reservoir layer incorporating the active material and a diffusion rate limiting layer on the front surface. The impermeable layer is described as a metal foil polymer laminate, wherein the polymer is selected from polyethylene terephthalate, polyethylene, polypropylene, polyvinyl chloride and ethylene vinyl acetate. The reservoir layer is made of a porous polymer, an impregnated polymer or a gelled polymer mixture.

U.S. Pat. No. 5,282,571 (Smith et al.) (Feb. 1, 1994) describes a plastic automobile sun visor clip, wherein the plastic material is impregnated with an aroma-creating material. The clip is molded via a combination of plastics, including a product described as POLYIFF, which is described as a fragrance impregnated plastic obtained from International Flavors and Fragrances, Inc.

U.S. Pat. No. 5,820,791 (Canale) (Oct. 13, 1998) describes an air freshening device to be used in conjunction with an air circulation system. The device is a molded object shown in one embodiment as a grid of rectangular intersecting plastic pieces, wherein the plastic is a combination of conventional plastic and scent impregnated plastic.

WO 03/097114 (Jean et al.) (Nov. 27, 2003) describes a molded thermoplastic article consisting of a decorative face and a plastic replaceable element that is impregnated with a volatile active ingredient such as a perfume. The resin of the element is a volatile impregnated polyether-ester-amide type plastic identified under the commercial name "PEBAX." The element is attached to a fixing system, which associates the device with a ventilation or air conditioning system.

U.S. Pat. No. 6,938,832 (Sada) (Sep. 6, 2005) describes a scent strip that is constructed with a back adhesive layer, a layer of porous material containing the active material and a peelable protective cover layer. The strip is intended to be adhered to a surface of an entertainment medium such as a DVD box and, upon cue from the medium, the cover is peeled off to release the volatile and thus enhances the entertainment experience.

US 2008/0105760 (Sheffield et al.) (May 8, 2008) describes an aromatic device having a volatile-impregnated decorative and/or shaped unit on a suction cup for adherence to a flat surface.

U.S. Pat. No. 7,159,792 (Wheatley et al.) (Jan. 9, 2007) describes an air freshener that can be removeably adhesively attached to a surface so as to be capable to locate and relocate where needed. The device consists of a scent portion and attachment portion. The scent portion contains an active carrier material, such as a polymer or polymer gel, that is free-standing and contains an active, such as scented oil. The polymer body is compressible under an applied force and substantially returns to its original shape when the force is removed. Polyurethane or polyurethane gel is described as an example of a carrier material. The attachment portion includes a pad formed of a material that imparts a "clingy, tacky or frictional quality," which provides surface adhesion. The shape and size of the scent portion can be configured to determine the amount and rate of scent release.

US 2009/0072045 (Wheatley et al.) (Mar. 19, 2009) describes an air freshener device having a head as described for the scent portion of U.S. Pat. No. 7,159,792 pivotally combined with a vent rod for insertion into a vehicle air vent.

US 2010/0065654 (Wheatley et al.) (Mar. 18, 2010) describes an air freshener device having a basic head as described for the scent portion of U.S. Pat. No. 7,159,792 and vent rod as described in US 2009/0072045. However, the device contains multiple rods and multiple heads which are arranged to form a decorative display.

US 2011/0108632 (Brandenburg et al.) (May 12, 2011) describes an air freshener clip that is removeably engaged with a louver or slat of a vent. The clip is constructed of a base plastic which is covered with an outer portion of a plastic that has been compounded with a fragrance material prior to injection molding.

US 2012/0067970 (Hossein) (Mar. 22, 2012) describes an air freshener having a support element and a decorative element associated with the support element. The support element is designed for insertion into a grille, and the decorative element has a thermoplastic polymer matrix that contains a scent agent to be spread to the environment. An example of the decorative element is one constructed of 70-72% by weight ethylene vinyl acetate and 28-30% scent agent. The support element may be detachable from the decorative element.

EP1704874 (Barthel et al.) (Sep. 27, 2006) describes an aroma dispenser constructed for attachment to vents of appliances such as a home computer. The dispenser contains an attachment portion that is arched when fitted to the appliance. Air exiting the vent passes through the arch into a receiving space containing a scent delivery system, consisting of spherical particles of a polymeric carrier material and a fragrance in the form of a perfume oil. An example of the carrier material is ELVAX 150 from DuPont. A loading of 30-35% is possible with the ELVAX 150. Methods for adhering the scent-dispensing portion to the fastener portion of the device include an adhesive layer and a Velcro fastener.

In spite of the various efforts to provide a fragrance release system described above, there remains a need for a fragrance release system that is economical and simple in construction and can be adapted to have utility in many environmental applications, and preferably, effectively provides a linear release of aromachemical over the lifetime of the article.

SUMMARY OF THE INVENTION

Thus, an objective of the present invention is to provide a basic structure of a fragrance release engine that is simple in design and requires no positive mechanical driven support within the engine.

A further objective of the present invention is to provide a fragrance release engine that is perceived to emit fragrance in a linear manner over the scheduled lifetime of the system.

Another objective of this invention is to provide a fragrance release engine that is simple in design and economical and can be adapted for use in most general environments, such as, an automobile or other commercial or personal vehicle, warehouse, washroom, public restroom, restroom in an airplane, train or ship, kitchen, bedroom, basement, utility room, garage, kennel or other facilities containing animal odor.

A further objective is to provide a fragrance release engine that is suitable for use in conjunction with or as part of an air filter of an air conditioning or heating unit in a residence, a commercial facility such as a hotel or a vehicle.

In another objective, the fragrance release engine may be adapted for use as a personal wear accessory such as a decorative fixture to be directly affixed to an article of clothing, a backpack, a gym bag, a purse or other such item. Additionally, the fragrance release engine may be incorporated into an item such as a pendant, bracelet or necklace.

These and other objectives, either individually or in combinations thereof, have been achieved according to the present invention, the first embodiment of which includes a multi-layer article, comprising:

a sorbent layer having a first side and a second side;

a vapor permeable or microporous layer adjacent to at least a portion of at least one of the first side and the second side of the sorbent layer;

optionally, a second vapor permeable or microporous layer on a side of the vapor permeable layer not adjacent to the sorbent layer;

optionally, a vapor impermeable layer adjacent to a portion of the sorbent layer not adjacent to the vapor permeable or microporous layer; and an active composition having at least one volatile component; wherein the sorbent layer comprises the active composition, and each layer is capable of being formed into a required shape or structure.

In a preferred embodiment, the multilayer article according to the first embodiment comprises the impermeable layer, wherein the vapor permeable layer is adjacent to the first side of the sorbent layer and the vapor impermeable layer is adjacent to the second side of the sorbent layer. In a preferred embodiment, the multi-layer article further comprises a base layer adjacent to the vapor impermeable backing layer; wherein the base layer is capable of being formed to a shape and once formed, maintain the shape.

In a further highly preferred embodiment the multi-layer article comprises a second vapor permeable or porous layer that provides a decorative design or form.

In a special embodiment, the sorbent layer comprises regular or irregular folds of the sorbent material and the vapor permeable or microporous layer envelopes the sorbent layer.

The present invention further provides a method for treating the atmosphere of an environment, comprising: placing the multilayer article according to the embodiments of the invention in the environment; and orienting the multilayer article to permeate at least one volatile component released from the vapor permeable or microporous layer throughout the environment; wherein the air in the environment is deodorized, freshened or both deodorized and freshened.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

The Figs. are schematic and are not intended to show actual dimensional relationships.

DETAILED DESCRIPTION OF THE INVENTION

Applicants have studied various configurations and structures of components and have discovered a unique and novel multi-layer structure that, when constructed in an article, meets one or more of the objectives described above.

Thus, the invention provides a multi-layer article, comprising:

a sorbent layer having a first side and a second side;

a vapor permeable or microporous layer adjacent to at least a portion of at least one of the first side and second side of the sorbent layer;

optionally, a second vapor permeable or microporous layer on a side of the vapor permeable layer not adjacent to the sorbent layer;

optionally, a vapor impermeable layer adjacent to a portion of the sorbent layer not adjacent to the vapor permeable or microporous layer; and an active composition having at least one volatile component;

wherein the sorbent layer comprises the active composition, and each layer is capable of being formed into a required shape or form.

Figure 1:
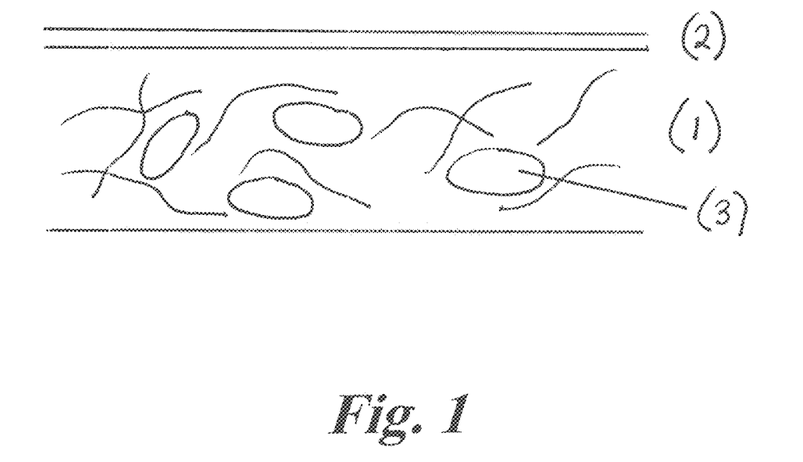
FIG. 1 shows a schematic drawing of the basic elements of the article according to the present invention.
Figure 4:
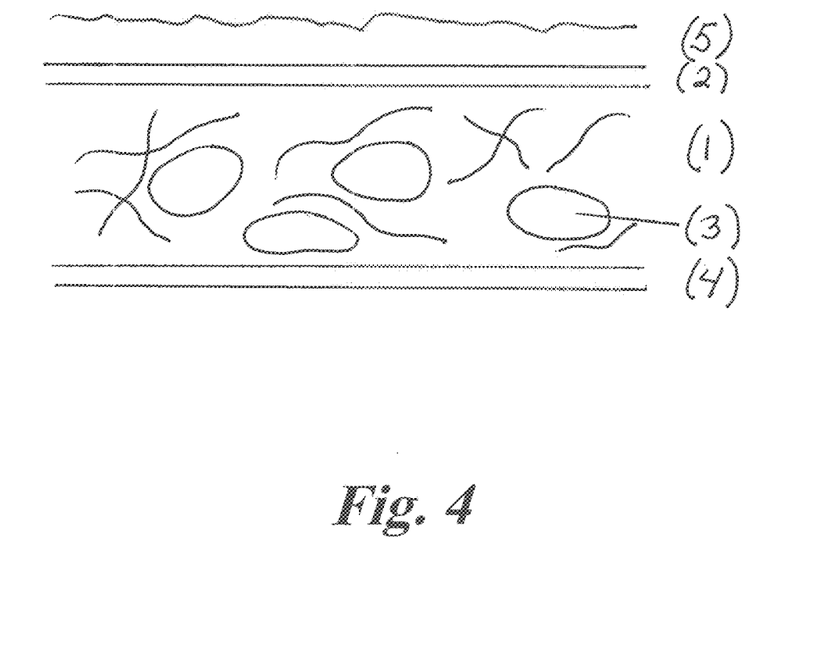
FIG. 4 shows another embodiment of the present invention wherein a decorative outer layer is included.

In one embodiment shown schematically in FIG. 1, the multi-layer article is constructed to have a sorbent layer (1) having a first side and a second side. Adjacent to the first side of the absorbent layer is a vapor permeable or microporous layer (2) that covers the absorbent layer, and, optionally, a second vapor permeable or microporous layer may be on the side of the vapor permeable or microporous layer not adjacent to the sorbent layer (FIG. 4, item (5)). Each of the layers is capable of being formed to assume various structural configurations, as may be required to render the article suitable or compatible for a particular application. According to the present invention, the element "capable of being formed into a required shape or form" describes that a layer may be shaped to optimize the form of the fragrance engine for a particular application. However, it is not a requirement of the invention that a layer have a specific shape or form, or a specific level of flexibility or rigidity. Suitable shapes may include, but are not limited to, planar, cubic, rectangular box, cylindrical, or any other desired shape. An active composition (3) having at least one volatile component is contained in the sorbent layer.

Figure 2:
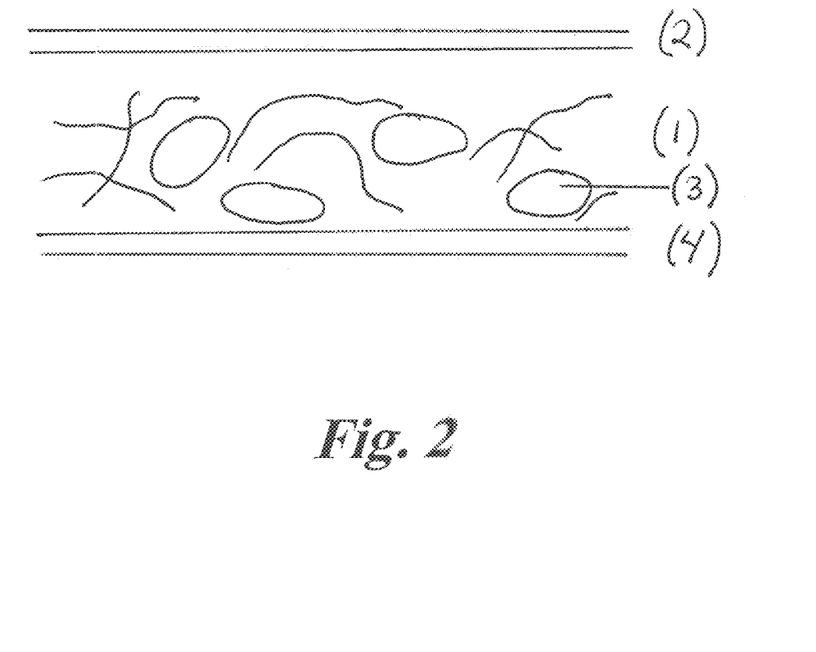
FIG. 2 shows a preferred embodiment of the article according to the present invention.

In another embodiment of the invention as shown in FIG. 2, a vapor impermeable layer (4) is adjacent to the second side of the sorbent layer. The vapor impermeable layer prevents emission of the volatile components present in the active composition of the sorbent layer from the second side of the article and retains the active composition within that layer. The vapor permeable or microporous layer also serves to retain the bulk of the active composition within the sorbent layer. However, based on the permeability or microporous construction of this layer, volatile components in the form of a vapor or microdispersed droplets can pass through this layer and thus enter the outside atmosphere.

The inventors have discovered that, by combining a sorbent layer containing an active composition compounded of volatile components having compatible vapor pressure and threshold values with a vapor permeable or microporous layer as according to the invention, it is possible to obtain a linear release of volatile materials, such as aromachemicals, over a prescribed performance lifetime.

The sorbent layer may be constructed of any absorbent material that is capable of containing an active composition and is chemically nonreactive with the components of the active composition. It may be constructed of both natural and synthetic fibers, and, in general, nonwoven layers having sufficient void space and resilience are preferred. Void space provides reservoir capacity for containing the active composition and may be correlated with the density of the material. The density may be from 2.0 to 25 mg/cc, preferably, 3.5 to 20 mg/cc, and, most preferably, 5.0 to 15 mg/cc.

The nonwoven fabrics of the sorbent layer may be thermally bonded nonwovens and, in a highly preferred embodiment, the nonwoven may contain a superabsorbent polymer that may enhance absorbency and retention of the active composition. Nonwovens suitable for utility in the multi-layered article of this invention may have a basis weight in the range of from 80 to 200 $g/m^2$, preferably 100 to 180 $g/m^2$, and most preferably 120 to 160 $g/m^2$. The caliper of the material may be from 0.2 to 100 mm, preferably, 0.5 to 10 mm, and most preferably, 1.0 to 5.0 mm. Suitable nonwoven fabrics according to the invention include products supplied by Georgia Pacific, EAM, McAirlaid and Buckeye.

The vapor impermeable backing layer (4) adjacent to the second side of the sorbent layer serves as "barrier" to fragrance migration from the second side of the fragrance release engine. This layer may be constructed of any material that is chemically inert to the active composition and is impermeable to vapors of the active composition. In preferred embodiments, the material of the backing layer may have sealant capability and may serve to seal the release engine to a base structure. At the same time the backing layer must prevent leakage of the active composition onto the base structure, thus preventing adverse interaction of the active composition with a substrate adjacent to the side of the impermeable layer opposite to the sorbent layer. For example, where the article is applied to a painted surface, leakage of the active composition onto the paint layer may cause peeling of the paint.

Materials suitable for utility as the vapor impermeable film may include laminates of LDPE/Polyester, LDPE/OPP, as well as films of EVA-Polyester, LDPE-Polyester and EVA-LDPE/Polyester. As ingredients contained in the active composition may adversely affect the chemical stability or physical properties of a given film, one of ordinary skill will understand that testing may be necessary to establish compatibility of the active composition and the vapor impermeable film, such that impermeability is maintained throughout the projected shelf and active article lifetime. Films, such as those marketed under the Mylar® brand, conventionally employed for food packaging may also be suitable. The impermeable backing film may be from 1.5 to 3.0 mil in thickness, preferably, 1.75 to 2.5 mil, and most preferably, 2.0 to 2.25 mil. In a preferred embodiment the barrier backing film may be an EVA backed polyester laminate supplied as a 2.05 mil film under the trade name EXCO Film 9733 by 3M ScotchPak.

In one embodiment of the invention, an adhesive may be applied to the side of the impermeable layer not adjacent to the sorbent layer. The adhesive may function to adhere the multi-layer article to a substrate such as a wall, an appliance, a dashboard, a pendent, an article of clothing or a personal accessory. The adhesive may be applied in a continuous layer or as adhesive tack spots, and may be a pressure sensitive adhesive. Optionally, the adhesive layer may be covered with a peelable sheet which is removed when the article is to be adhered to a substrate.

The semipermeable or microporous film adjacent to the side of the sorbent layer serves to prevent migration of active composition oils from the sorbent layer, as such weeping is detrimental to performance and attractiveness of the fragrance article. At the same time, the semipermeable or microporous film allows passage of vapors or microdispersed droplets of the active composition from the sorbent layer into the exterior atmosphere. The inventors have surprisingly discovered that, by selection of a suitable combination of sorbent, active composition and semipermeable or microporous film, a linear release of aromachemicals over a selected scheduled lifetime of a fragrance release engine may be achieved. This is particularly surprising because conventional wisdom would expect that the presence of such a semipermeable or microporous film would inhibit emission of vapors or dispersed microdroplets.

Materials suitable for utility as the flexible semipermeable or microporous film may include LLDPE, EVA, LLDPE/EVA co-polymers and LLDPE/EVA/EEA co-polymers. The film preferably may have a mass density in the range of from 10 to 40 g/m$^2$, preferably 12 to 30 g/m$^2$, and most preferably 14 to 20 g/m$^2$. In a preferred embodiment, the flexible microporous film is a film sold under the trade name DH267 PE Clear 120 which has a basis weight of 16.4 g/m$^2$, supplied by Clopay.

As indicated above, the vapor impermeable film is an optional element of the multi-layered article and in some embodiments, the vapor impermeable film may not be present. In an embodiment having no impermeable film, the sorbent layer may be enveloped by a vapor permeable film or a combination of vapor permeable films. In a preferred embodiment, the sorbent layer may be multiply folded or wound, either in a regular or irregular pattern to increase or maximize capacity for the active composition. The multiply folded sorbent layer may be encased or enveloped with the vapor permeable film and optionally a decorative layer applied thereon.

Optionally, a decorative outer layer (5) (FIG. 4) may be placed on the side of the semipermeable or microporous film (2) not adjacent to the sorbent layer. The decorative outer layer is constructed of a material that can be formed into a required shape or structure and that allows passage of the vapor or dispersed microdroplets, which emit through the semipermeable or microporous film to the external environment. Materials suitable as decorative layer may include any nonwoven or porous film that can be pigmented, colored, embossed, debossed and otherwise decorated as conventionally known. Alternatively, a perforated film may be employed as the decorative layer.

In a highly preferred embodiment of this invention (FIG. 3), the fragrance release engine is affixed to a base component (6) on the impermeable film side. This base may be of any form and is designed to impart a structure by which the fragrance delivery system may be conveniently attached or positioned in a location within or accessible to the environment space to which emission of the components is intended.

Figure 3:
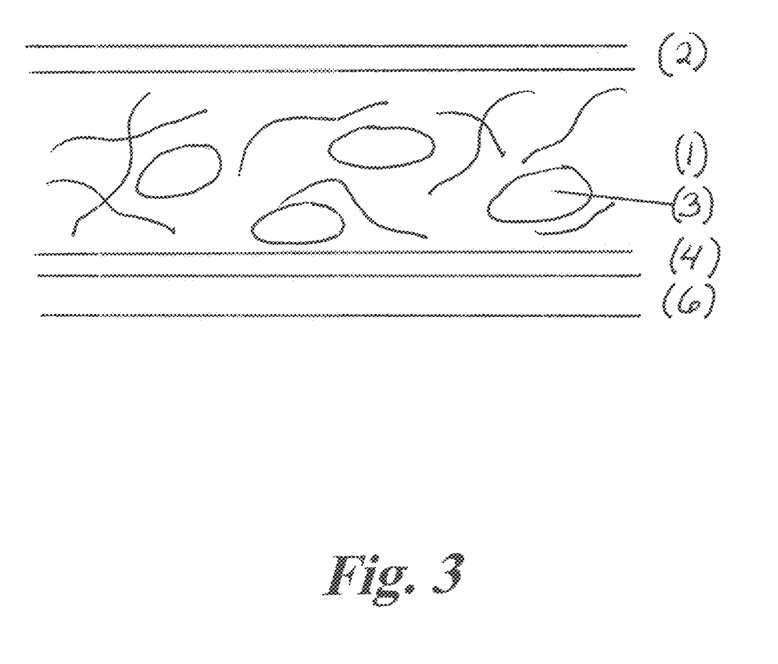
FIG. 3 shows another embodiment of the present invention where the article is on a molded plastic base.

The base component may be of a fixed shape designed, for example, for attachment to an appliance, a fixture, a structure within the passenger compartment of a vehicle or a heating/air conditioning vent. Alternatively, the base may be constructed of a flexible material that may be shaped by a consumer to fit within or affix to a projection or aperture within the space to be treated with the active composition.

The base may be formed of any natural or synthetic material suitable for the overall design and intended function of the fragrance release article, as long as it is compatible with the fragrance contained in the active composition. Materials that may be suitable as a base may include polyolefins, such as LDPE, HDPE, polypropylene, polycarbonates, nylons and polyesters. Materials based on styrene and acrylonitrile butadiene styrene (ABS) are generally not suitable for use as the base.

Figure 5:
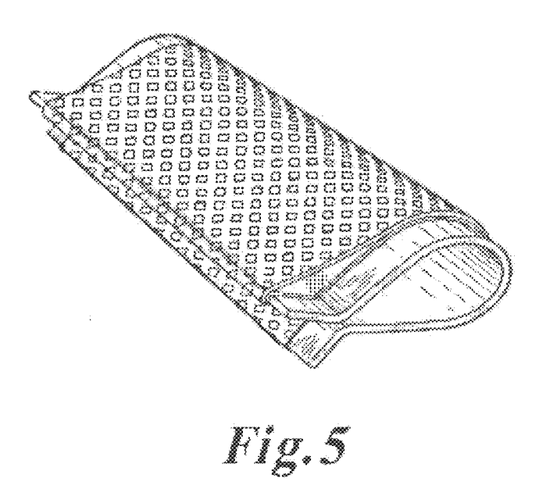
FIG. 5 shows a vent clip commercial embodiment according to the present invention.

An example of one embodiment which may illustrate the applicability of the present invention is shown in FIG. 5 and is described in U.S. Design application Ser. No. 29/441,071, filed Dec. 31, 2012.

In a preferred embodiment according to the present invention, a base may be constructed of LDPE, having a thickness of from 0.012 to 0.50 inches which may be of natural color, pigmented or colored.

The active composition contained in the sorbent layer may contain any of active ingredients, solvents, dispersants and volatilization assistants known to one of ordinary skill in the industry. In addition, other conventionally known additives that may impart specific physical properties to the active composition to optimize performance in a particular application may be incorporated in the active composition. Properties that may be optimized to obtain linear release for a selected article lifetime include but are not restricted to wetting, surface tension, interfacial tension and viscosity.

In general, ingredients having a vapor pressure of 0.03 to 2 mm Hg when measured at 20° C. and 760 mm Hg constitute at least 60% of the total weight of the active composition. Preferably, at least 70%, and most preferably, at least 80% by weight of the active composition is due to ingredients having a vapor pressure of 0.03 to 2 mm Hg. As known to one of ordinary skill in the art of perfumery, the ingredients compounded in the active composition may be selected based on vapor pressure and threshold values that are compatible and consistent with the prescribed lifetime, scent to be provided and consistency of that scent. Consistency or linear release may be evaluated by analytical chemistry methods, such as gas chromatography or by a panel of persons selected for olefactory perception skills. As indicated above, the inventors have discovered that providing a properly selected semipermeable or microporous film contingent to the sorbent layer serves to enhance the linearity of the scent perception obtained with a preferred embodiment of the fragrance release engine of the present invention.

In addition to volatile aromachemicals, the active composition may contain solvents that not only provide for a homogeneous liquid by dissolution of the composition components but also modulate the speed of evaporation of the active ingredients to the surrounding environment. Such solvents may belong to any of the families of isoparaffins, paraffins, hydrocarbons, glycols, glycol ethers, glycol ether esters, esters and ketones. Examples of commercially available solvents of these types include isoparaffins, Isopar® H, J, K, L, M, P or V (Exxon Chemical); dearomitised hydrocarbons, Exxsol® D 155/170, D 40, D 180/200, D 220/230, D 60, D 80, D 100, D 110 and D 120 (Exxon Chemical); glycol ethers, Dowanol® PM. TPM, PnB, DPnB, TPnB, PnP and DPnB (Dow Chemical Compant); glycol ether esters, Dowanol® PMA and PGDA (Dow Chemical Compan), and Eastman® EB acetate, Eastman® DE acetate, Eastman® DB acetate, Eastman® EEP acetate. Other suitable solvents include dipropylene glycol, propylene glycol, ethylene glycol ethyl ether acetate, ethylene glycol diacetate, isopropyl myristate, diethyl phthalate, 2-ethylhexyl acetate, methyl n-amyl ketone and di-isobutyl ketone.

Commercial active compositions may be obtained from fragrance producers such as Givaudan, Firmenich, IFF, Mane, Takasago and Agilex. These compositions may contain any additives conventionally employed in the fragrance industry and may be pre-compounded with solvents and carriers that support or enhance linear release.

The multilayer article, according to the present invention, may be constructed by conventional methods for producing multi-layer units known to one of ordinary skill in the art. In one embodiment, the sorbent layer is cut to size and placed adjacent to a vapor impermeable film as unwound from a supply roll. The sorbent layer may not be fixed to the vapor impermeable film but merely mechanically held in place, or the sorbent layer may be adhered to the vapor impermeable film with an adhesive layer or tacking with an adhesive. The vapor permeable film is applied to the side of the sorbent layer in a similar manner. If the optional decorative layer is included, the decorative layer may be in a predecorative form when applied or decorated after the multi-layer article is constructed.

The semipermeable or microporous film is applied adjacent to the sorbent layer opposite to the vapor impermeable layer and the optional decorative film placed over the semipermeable or microporous film. The vapor permeable layer may be heat or pressure sealed, preferably at peripheral edges, to the sorbent layer. Such sealing may be achieved by methods generally known in the industry, including, for example, impulse sealing, ultrasonic sealing or pressure bonding with a pattern. In a preferred embodiment, the layers are bonded with a patterned pressure bond having from 25 to 50% of the bond surface area occupied by the bond pattern.

The fragrance delivery article according to the invention may be applied to a formed base either by sealing with the impermeable backing film or by application of an adhesive layer between the impermeable backing film and the base. Adherence of the fragrance delivery article to a base may be achieved by any of the conventional methods of lamination known to one of ordinary skill in the art.

The present invention also provides a method to treat or deliver fragrance to an environment. As one can recognize from the foregoing description, the multi-layer article according to the present invention may be provided in large variety of shapes and configurations and in a wide range of sizes. With respect to size, the multi-layer article may vary from relatively small such as a button-size to large panel-like structures, such as 4 ft×8 ft sheets. The former application is of utility for personal use, while the latter may be placed in a large compartment such as a warehouse. The environment may also be a localized space such as the space within a gym bag or purse. Alternatively the localized space may be a section of a hallway or other localized space not necessarily confined by walls or structure.

In general the method for treating the atmosphere of the compartment includes placing the multi-layer article according to the present invention in the compartment or at the location to be treated and orienting the article so that the volatile material that is released from the vapor permeable or microporous layer enters the area to be treated. Such treatment may include freshening the atmosphere or deodorizing the area or both freshening and deodorizing.

While multiple embodiments of the present invention have been described in the foregoing paragraphs one of skill in the art will recognize that various and further modifications may be made to the multi-layer article as described in this specification and in the Claims without departing from the basic structure and elements of this invention. All such embodiments are intended to fall within the scope of the present invention.

The invention claimed is:

1. A multi-layer article, comprising:
a sorbent layer having a first side and a second side;
a vapor permeable or microporous layer adjacent to at least a portion of at least one of the first side and second side of the sorbent layer;
optionally, a second vapor permeable or microporous layer on a side of the vapor permeable layer not adjacent to the sorbent layer;
optionally, a vapor impermeable layer adjacent to a portion of the sorbent layer not adjacent to the vapor permeable or microporous layer; and
an active composition comprising at least 60% by weight of at least one volatile component having a vapor pressure of 0.03 to 2 mm Hg when measured at 20° C. and 760 mm Hg;
wherein
the sorbent layer is a nonwoven material having a density of from 2.0 to 25 mg/cc,
the sorbent layer comprises the active composition, and
each layer is capable of being formed into a required shape or structure.

2. The multi-layer article, according to claim 1, which comprises the vapor impermeable layer;
wherein
the vapor permeable or microporous layer is adjacent to the first side of the sorbent layer; and
the vapor impermeable layer is adjacent to the second side of the sorbent layer.

3. The multi-layer article according to claim 2, further comprising a base layer adjacent to the vapor impermeable layer;
wherein
the base layer is capable of being formed to a shape and, once formed, maintain the shape.

4. The multi-layer article according to claim 3, wherein the base layer is formed as a clip to pinch fix onto an object.

5. The multi-layer article according to claim 4, wherein the period of release time is from 1 to 8 weeks.

6. The multilayer article according to claim 4, wherein at least a portion of the object comprises a slat shape to which the multilayer article is pinch fixed.

7. The multi-layer article according to claim 3, further comprising an adhesive layer between the base layer and the impermeable layer; and optionally comprising adhesive peripheral bands or tacks between any other adjacent layers.

8. The multi-layer article according to claim 2, wherein the vapor impermeable layer is a barrier film that is inert to the active composition and provides a seal to the second side of the sorbent layer.

9. The multi-layer article according to claim 8, wherein the barrier film is selected from the group of films consisting of an ethylene vinyl alcohol (EVA) polyester laminate, a low-density polyethylene (LDPE) polyester laminate and a EVA-LDPE polyester laminate.

10. The multilayer article according to claim 2, further comprising an adhesive layer on a side of the vapor impermeable layer opposite to the side adjacent to the second side of the sorbent layer.

11. The multilayer article according to claim 10, wherein the adhesive of the adhesive layer is a pressure sensitive adhesive or the adhesive is covered with a peelable sheet.

12. The multi-layer article according to claim 1, further comprising the second vapor permeable or microporous layer; wherein the second vapor permeable or microporous layer comprises a decorative design or form.

13. The multilayer article according to claim 1, wherein the non-woven material of the sorbent layer is inert to the active composition and has a capacity for the active composition while allowing for release of volatile components or a mist of the active composition through the vapor permeable or microporous layer or layers.

14. The multi-layer article according to claim 13, wherein the density of the non-woven material is from 3.5 to 20 mg/cc.

15. The multi-layer article according to claim 13, wherein the non-woven material comprises a superabsorbent polymer that increases the capacity for the active composition.

16. The multi-layer article according to claim 1, wherein the active composition having at least one volatile component comprises:
   a mixture of aromachemicals; and
   a carrier;
   wherein
   the aromachemicals of the mixture each has a vapor pressure and a threshold for human olfactory detection, and
   a release rate of the aromachemical composition of the mixture is such that the fragrance is perceived to be linear over a selected period of release time.

17. The multi-layer article according to claim 16, wherein the vapor pressure of each aromachemical component is from 0.03 to 2 mm Hg at 20° C. and 760 mm Hg atmospheric pressure.

18. The multi-layer article according to claim 1, wherein the vapor permeable or microporous layer contingent to the sorbent layer is a thin film of a material selected from the group consisting of linear low density polyethylene (LLDPE), ethylene vinyl alcohol (EVA), ethylene ethyl acrylate (EEA) and mixtures thereof.

19. The multi-layer article according to claim 18, wherein a weight of the vapor permeable or microporous thin film is less than 20 g/m$^2$.

20. The multilayer article according to claim 1, wherein the sorbent layer comprises regular or irregular folds of the sorbent material and the vapor permeable or microporous layer envelopes the sorbent layer.

21. The multilayer article according to claim 1, wherein the vapor permeable or microporous layer is adjacent to both the first side and the second side, and wherein the vapor permeable or microporous layer adjacent to the first side may be the same as or different from the vapor permeable or microporous layer adjacent to the second side.

22. A method for treating the atmosphere of an environment, comprising:
   placing a multilayer article in the environment to be treated; and
   orienting the multilayer article to permeate at least one volatile component released from the vapor permeable or microporous layer throughout the environment to obtain a deodorized and/or freshened environment;
   wherein
   the multilayer article comprises:
   a sorbent layer having a first side and a second side;
   a vapor permeable or microporous layer adjacent to at least a portion of at least one of the first side and second side of the sorbent layer;
   optionally, a vapor impermeable layer adjacent to a portion of the sorbent layer not adjacent to the vapor permeable or microporous layer; and
   an active composition comprising at least 60% by weight of at least one volatile component having a vapor pressure of 0.03 to 2 mm Hg when measured at 20° C. and 760 mm Hg;
   wherein
   the sorbent layer is a nonwoven material having a density of from 2.0 to 25 mg/cc and comprises the active composition.

23. The method according to claim 22, wherein the environment is a compartment or a localized space.

* * * * *

UNITED STATES PATENT AND TRADEMARK OFFICE
CERTIFICATE OF CORRECTION

| | | |
|---|---|---|
| PATENT NO. | : 8,968,647 B2 | Page 1 of 1 |
| APPLICATION NO. | : 13/734139 | |
| DATED | : March 3, 2015 | |
| INVENTOR(S) | : Albert M. Fischer et al. | |

It is certified that error appears in the above-identified patent and that said Letters Patent is hereby corrected as shown below:

On the title page, item (71) should read:
(71) Applicants: JULIUS SÄMANN LTD., Hamilton (BM)

On the title page, item (72) Inventors:
change the fourth inventor's address from "Admas, NY (US)" to --Adams, NY (US)--

Signed and Sealed this
Third Day of November, 2015

Michelle K. Lee
*Director of the United States Patent and Trademark Office*